United States Patent [19]

Fletcher, III

[11] 4,033,830

[45] July 5, 1977

[54] ON-LINE AMPEROMETRIC ANALYSIS SYSTEM AND METHOD INCORPORATING AUTOMATIC FLOW COMPENSATION

[75] Inventor: Kenneth S. Fletcher, III, Norfolk, Mass.

[73] Assignee: The Foxboro Company, Foxboro, Mass.

[22] Filed: Mar. 17, 1976

[21] Appl. No.: 667,969

[52] U.S. Cl. .......................... 204/1 T; 73/194 EM; 204/195 R; 324/29
[51] Int. Cl.[2] ........................................ G01N 27/54
[58] Field of Search ............... 204/1 B, 1 T, 195 R; 324/34 FL, 29; 73/194 EM

[56] References Cited

UNITED STATES PATENTS

| | | | |
|---|---|---|---|
| 3,341,430 | 9/1967 | Wickersham et al. ................ | 204/1 |
| 3,402,116 | 9/1968 | Kaltenhauser et al. ........ | 204/1 B X |
| 3,449,233 | 6/1969 | Morrow .......................... | 204/1 B X |
| 3,479,873 | 11/1969 | Hermanns .................... | 73/194 EM |
| 3,621,381 | 11/1971 | Eckfeldt .................... | 204/195 R X |
| 3,664,191 | 5/1972 | Hermanns .................... | 73/194 EM |
| 3,959,087 | 5/1976 | Morrow ............................ | 204/1 B |
| 3,960,673 | 6/1976 | Morrow ...................... | 204/195 R X |

OTHER PUBLICATIONS

M. K. Bevir, *Measurement and Control*, vol. 3, No. 12, pp. T193–196 (1970).

Henry C. Marks et al., *Analytical Chem.*, vol. 19, No. 3, pp. 200–204 (1947).

*Primary Examiner*—G. L. Kaplan
*Attorney, Agent, or Firm*—Parmelee, Johnson & Bollinger

[57] ABSTRACT

An amperometric analysis system and method includes a flow tube constituting the amperometric cell in which magnetic flow metering electrodes function also as the counter and test electrodes for amperometric measurement. By combining the magnetic flow measurement with the amperometric measurement, additional electrodes are not needed to obtain the flow signal for compensating the amperometric measurement. Ultrasonic drivers are mounted on the end of the shank of the counter and test electrodes and driven by an ultrasonic oscillator to activate the electrodes to keep them clean. Complementary cleaning can be obtained through the simultaneous application of an electrochemical anodic pulse. The system includes a three-electrode circuit potentiostat in which the potential of the test electrode is fixed versus a reference electrode and the current flows between the test electrode and the counter electrode. An isolated current source allows the magnetic flow metering electrodes to serve simultaneously as test and counter electrodes in the amperometric circuit. The flow tube also includes a thermistor temperature compensator. Reliable direct amperometric analysis of a flowing stream is made possible by the invention.

10 Claims, 3 Drawing Figures

ON-LINE AMPEROMETRIC ANALYSIS SYSTEM AND METHOD INCORPORATING AUTOMATIC FLOW COMPENSATION

BACKGROUND OF THE INVENTION

This invention relates to amperometric measurement of a chemical in a flowing process stream. More particularly, this invention relates to an amperometric analysis method and system having process stream flow rate and temperature compensation. Advantageously, the system electrodes may be both ultrasonically cleaned and cleaned by electrochemical anodic pulse to provide a more reliable indication of stream concentration.

Amperometric methods of analysis to produce a current proportional to the concentration of the material measured have been known and applied in various industrial processes. See, for example, Smith, D. E. and Zimmerli, F. H., "Electrochemical Methods Of Process Analysis," ISA (1972), pp. 153–160. The amperometric measurement technique is based on the electrochemical oxidation or reduction of certain chemical species at the surface of suitable electrodes immersed in the solutions under test. The oxidation or reduction reaction involves the transfer of electrons between the chemical species and the electrode, thereby inducing a current flow. By selection of the appropriate applied potential, the particular species to be measured can often be selected.

The limiting current, that is, the maximum current for the reaction at the applied potential selected for the amperometric measurement for the component of interest, is linearly related to the concentration at fixed fluid velocity and temperature. Empirical studies demonstrate that the limiting current shows a temperature sensitivity of about +1.5 percent per degree centigrade and a linear relationship to approximately the cube root of hydrodynamic flow velocity.

While amperometry can be a sensitive and selective method for the direct measurement of "electroactive" materials, its use as such has been limited, finding primary application in amperometric titrations where amperometry is used indirectly to detect the appearance or disappearance of an electroactive substance which signals a titration endpoint.

The limited utility of amperometric analyzers as reliable direct chemical sensors can be attributed to several factors. Since the output current is a function of fluid flow, this has necessitated controlling the process flow, an often difficult task where it is desired to measure a process stream in as representative a fashion as possible. Also of significance is the loss of sensitivity of the instrument with time as the electrode becomes coated with insulating films. Since the measurement signal is derived from the flux of electrons across the electrode-solution interface energy barrier, any coating or deposit there can affect the measurement either by changing the flux by physical blockage of the electrode area or by synergistic chemical and physical effects on the active surface sites.

A prior art attempt at overcoming the latter aforementioned problem involves cleaning the surfaces of electrodes within a sensing cell by the continuous action of plastic balls pushed by a synchronous motor driven rotating striker. The action of the balls against the electrodes is said to maintain a constant level of cleanliness, thus eliminating drift while a thermistor may compensate for temperature variation in the sample. While such an amperometric analyzer is suggested, by the manufacturer, for continuous analysis of free or total chlorine residual in water, nevertheless, this approach involves the use of moving components and the mechanical difficulties of breakdown and maintenance associated therewith and still fails to achieve maximum reliability.

SUMMARY OF THE INVENTION

In accordance with one aspect of this invention certain disadvantages previously associated with direct amperometric measurement of process stream concentration are overcome by measuring the flow and using this measurement to automatically and directly compensate the amperometric measurement. The apparatus further includes means for ultrasonically cleaning the amperometric electrodes to prevent buildup of insulating deposits, thereby to maintain the desired accuracy over long periods of time. Complementary cleaning may be obtained by application of an electrochemical anodic pulse simultaneous with the application of the ultrasonic energy. An instrument which is more reliable than previous devices is obtained.

In accordance with a more specific aspect of the invention, the amperometric analysis system includes a flow tube constituting an amperometric cell in which one set of electrodes serves both as the counter and test electrodes needed for amperometric measurement and as magnetic flow metering electrodes. By combining amperometric measurement and magnetic flow measurement apparatus an improved overall arrangement is created for developing a compensated amperometric measurement. Ultrasonic electrode drivers are mounted on the end of the shank of the counter and test electrodes and driven by an ultrasonic oscillator to activate the electrodes with sufficient amplitude to remove, and maintain them free of the insulating accumulation that can occur in industrial applications. Where the ultrasonic cleaning to remove plated deposits would require application of energy at levels which might result in electrode surface erosion, this invention provides a complementary cleaning procedure utilizing the application of an electrochemical anodic pulse simultaneous therewith.

The amperometric analysis system and method according to this invention includes a potentiostat configuration of electrodes having a three-electrode circuit in which the potential of the test electrode is automatically maintained at a preset value relative to that of a reference electrode, by a feedback control system which continuously controls the current flow between the test electrode and the auxiliary or counter electrode. An output signal is developed proportional to this electrode current, as an indicator of the concentration of the chemical being monitored. The preferred potentiostat uses an isolated current source for the test electrode, and the isolation arrangement is such as to facilitate using the electrodes simultaneously as test and counter electrodes in the amperometric circuit, and as magnetic flow metering electrodes. The circuitry for developing the final output signal also advantageously provides temperature compensation.

Accordingly, a feature of this invention is the provision of an amperometric analysis system and method which measures flow to provide a flow signal for use in compensating the amperometic measurements.

A further feature of this invention is the provision of an amperometric analysis system and method in which a flow tube having magnetic flow metering electrodes simultaneously serves as an amperometric cell with test and counter electrodes in an amperometric circuit.

Yet another feature of this invention is the provision of an amperometric analysis system and method utilizing electrodes cleaned ultrasonically and by anodic pulse.

A fuller understanding of the advantages and features of this invention will be had from the following detailed description considered together with the accompanying drawings.

DETAILED DESCRIPTION OF THE DRAWINGS

Figure 1:
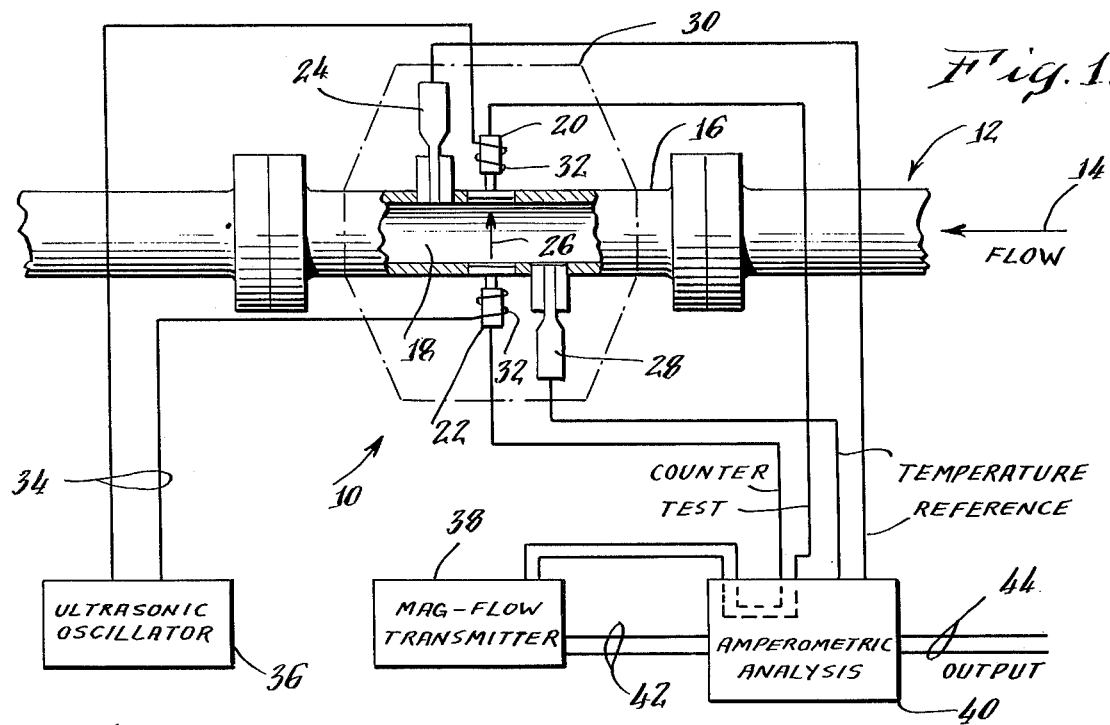
Figure 2:
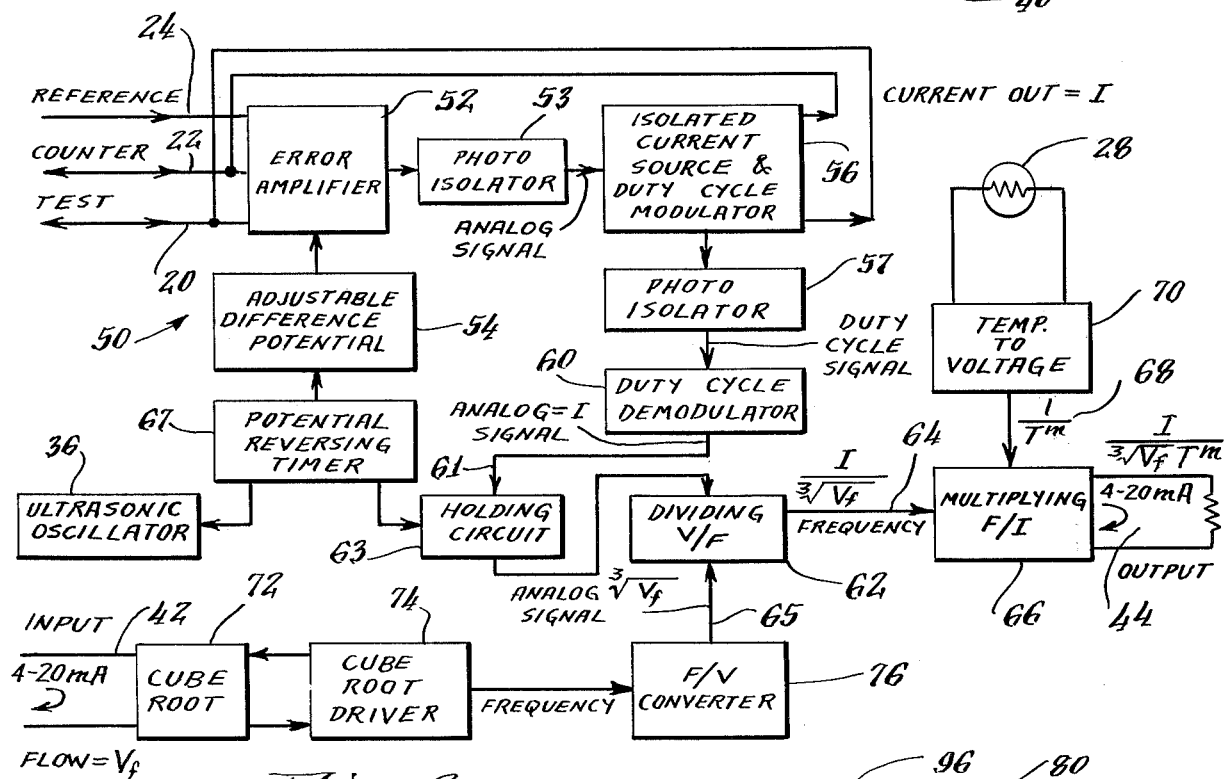
Figure 3:
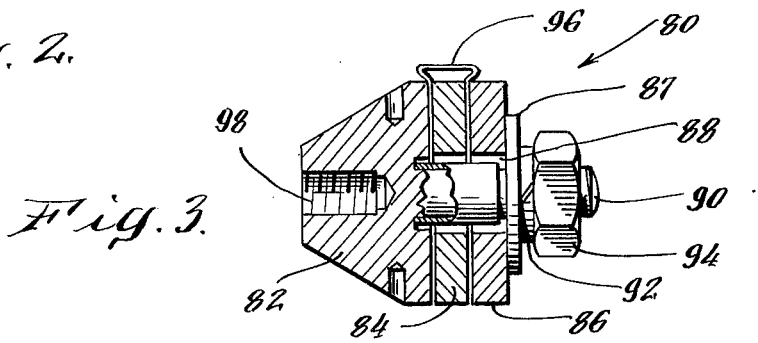

FIG. 1 is a schematic view of an amperometric analysis system according to an embodiment of this invention;

FIG. 2 is a schematic block diagram of a preferred system, particularly illustrating the potentiostat used in amperometric analysis in such a way as to enable simultaneous use of a set of electrodes both as magnetic flow metering electrodes and as counter and test electrodes; and FIG. 3 is a sectional view of a piezoelectric driver for mounting on the electrode shaft for ultrasonic cleaning according to an embodiment of this invention.

DESCRIPTION OF THE PREFERRED EMBODIMENT

Referring to FIG. 1, there is shown an amperometric analysis system 10 in connection with a process stream or sample line conduit 12, containing material the concentration of which is to be determined and flowing in the direction shown by the arrow 14. The amperometric analysis system includes a flow tube 16 mounted in the line 12 and defining an amperometric measurement cell 18. Positioned within the cell 18 are three electrodes, including two electrodes 20 and 22 which serve both as magnetic flow meter electrodes and as test and counter or auxiliary electrodes, respectively, of an amperometric measurement circuit, and a reference electrode 24.

These electrodes 20, 22, 24 form a potentiostat circuit in which the potential of the test electrode 20 is maintained at a pre-set differential relative to the reference electrode 24, by means providing for automatic adjustment of the current flow, as shown by the arrow 26, between the test electrode and the auxiliary or counter electrode 22. A temperature sensor 28, such as a thermistor temperature bulb, is also mounted in the flow tube 16. While the illustration in FIG. 1 is schematic, it is to be understood that the components may be arranged, according to the scheme shown, in a flow tube spool piece and covered with a housing 30 for direct placement in a process stream flow line as is known for magnetic flow transmitters. (Note: To simplify the drawings, the magnetic flowmeter structure is only partially shown; for example, the standard 60 Hz magnetic coils have been omitted.)

Mounted on the shafts of the test electrode 20 and the counter electrode 22 are ultrasonic driving elements 32 which are connected through ultrasonic power connections 34 to an ultrasonic oscillator 36. The nature of the ultrasonic driving elements 32 will be explained in greater detail in reference to FIG. 3.

The electronics required for the necessary measurements and compensations are shown in FIG. 1 as a block 40 representing that which is shown in FIG. 2 in greater detail. In addition, in FIG. 1 there is shown a block 38 labeled MAG FLOW TRANSMITTER comprising the usual flow-to-current converter. The magnetic flow measurement signal appears on lines 42 to be combined with the amperometric measurement signal and temperature compensation signal to develop at 44 an output current representing concentration and providing a signal for process monitoring and/or control, by known means.

FIG. 2 illustrates in more detail the circuitry used for the potentiostat arrangement 50 which as disclosed above allows the magnetic flow electrodes 20, 22 to serve simultaneously as the test and counter electrodes in the amperometric circuit. The function of the potentiostat is to supply current between the test and counter electrodes in such an amount that the potential difference between the test and reference electrodes is maintained at a pre-set value. Where the counter and test electrodes are also the magnetic flow electrodes, minimum interference with the magnetic flow signal is achieved by using an isolated current source 56 as shown.

Various different circuits and circuit components can be used for the potentiostat 50. A preferred circuit arrangement selected for an instrument which has been constructed and tested comprises an error amplifier 52, an adjustable reference voltage source 54, and the isolated current source 56. Isolation of the signal from the error amplifier 52 to the current source 56 is achieved in analog fashion, e.g., using a known photo isolator 53, so that no a-c signals which could upset the magnetic flow meter instrument are associated with the electrode circuits. A flow-responsive d-c signal derived from the magnetic flow electrodes and associated transmitter circuitry appears on leads 42. Temperature compensation is effected by the signal from a thermistor temperature bulb 28 mounted in the flow line.

The internal arrangement of the current source module 56 can use various different circuit devices to develop a current signal suitable for the electrodes. In one preferred arrangement, the current source module includes a known duty-cycle modulator producing a cyclic pulse-type signal wherein the ratio of the pulse on-time to the pulse off-time is proportioned to the error signal from the photo isolator 53, which signal in turn is proportional to the current to be supplied to the test electrode. Another photo isolator 57 receives the output of the modulator and directs a corresponding signal to a demodulator 60 which recreates the required d-c signal provided as an input to a known type of dividing voltage-to-frequency converter 62. Other types of dividers could of course be employed, but one utilizing a frequency-type signal affords certain advantages.

An analog signal derived from the magnetic flow signal 42 also is fed to the converter 62, as the divisor. This signal corresponds to a mathematical root of the flow rate, preferably approximately the cube root thereof, and in the disclosed embodiment is obtained from a circuit arrangement comprising three modules: a cube root module 72, a driver module 74 and a frequency-to-voltage converter 76. The cube root module may be developed in various ways, as are known for developing mathematical functions of this kind, e.g., such devices as are commonly used in root extractions. The driver 74 functions with the cube root module 72 to produce a cube root signal for the converter 76 the output of which is an analog signal 65 proportioned to $\sqrt[3]{V_f}$.

The final 4–20 mA output signal is generated by a multiplying converter 66, e.g., of the frequency-to-current type. One input of this device is the frequency signal $I/V_f^{1/3}$ at 64. The other input is an analog signal $1/T^m$, referred to at 68, generated through known techniques by a resistance-to-temperature converter module 70 in association with the resistance bulb sensor 28. The final output current 44 is thus proportional to the product $I/V_f^{1/3}T^m$ including both flow and temperature compensation.

The analog current signal 68 from the temperature compensation converter module 70 decreases with increasing process stream temperature. Thus, with a constant input frequency signal 64, the output current would decrease with temperature. However, the actual input frequency is proportional to the flow-compensated electrode current since it is the signal from the dividing voltage-to-frequency converter 62 having as the dividing input an analog signal proportional to the cube root of the flow signal. Thus, the output current 44 is temperature and flow compensted and proportional to the desired concentration of the unknown material in the process stream. These flow and temperature corrections could also be performed using a microprocessor.

The flow tube, magnetic flow electrodes and magnetic flow transmitter elements utilized herein may be obtained commercially such as those identified as the 2800 Series in product bulletin E-10C of The Foxboro Company, Foxboro, Mass. These may be provided with electrode ultrasonic cleaning as identified in general specifications sheet GS 1-6B5G of The Foxboro Company.

The ultrasonic cleaning consists of ultrasonic drivers installed on the electrodes and the ultrasonic oscillator with shielded cable which connects the oscillator to the driver on the electrodes. The high frequency movement of the drivers causes cavitation of the process fluid which keeps the sensitive portion of the electrodes clean, thus maintaining full sensitivity of the electrodes and minimizing manual cleaning requirements.

The ultrasonic oscillator is designed to supply power to drive a piezoelectric transducer, the electrode driver, at frequencies as determined by the resonant frequency of the transducer. The oscillator is designed for continuous operation, thus eliminating process interruption for periodic electrode cleaning.

FIG. 3 illustrates an ultrasonic electrode driver suitable for use with the electrodes of the amperometric analysis system of this invention to obtain ultrasonic cleaning of the electrodes and thus provide a reliable analysis. An ultrasonic cleaner which may be satisfactorily utilized herein is of the type utilized with magnetic flow meters with the power output of the oscillator being increased for amperometric analysis. Thus, the electrode driver 80 meets both acoustic requirements and space limitations.

Referring to FIG. 3, it is seen that the driver unit 80 is a simple arrangement of a base piece 82, a piezoelectric ceramic element 84 and a backup plate 86. The ceramic element 84 has an opening 88 at its center and, along with the backup washer plate 86, is assembled on a threaded stud 90 which is an extension of the base. The assembly is clamped tightly and held by combination of a washer 87, a lock washer 92 and a nut 94. Electrical connection to the ceramic element faces and electrical shielding and insulation from the rest of the structure is accomplished by a flexed circuit using an etched copper polyimide laminate, referred to generally at 96. A threaded opening 98 in the base piece 82 fits the electrode shaft.

The conical shape of the base 82 is designed to provide some acoustic impedance matching between the ceramic element 84 and the shaft of the electrode. The oscillator 36, FIG. 1, is intermittently coupled to the electrodes through a low capacitance cable 34.

Ultrasonic cleaning of an electrode surface depends on local cavitation at the electrode-solution interface which is the result of the rapid formation and violent collapse of infinitesimal bubbles which create extremely high pressure changes. These pressure changes produce mechanical shocks which result in the desired cleaning action. In some instances, it is possible that the electrode surface may become eroded due to the application of high ultrasonic energy to the transducer. This is undesired since an ill-defined electrode surface may affect the amperometric measurement.

In the event that the use of ultrasonic cleaning becomes unsatisfactory due to the fact that the energy required to remove deposits plated on the electrode may lead to the general erosion of the electrode surface, a complementary cleaning procedure involving the application of an electrochemical anodic pulse simultaneous with the application of ultrasonic energy may be used. For example, a positive potential can be applied to the test electrode 20 for brief intervals to strip off plated deposits electrochemically. Where the test electrode is comprised of platinum, and hence is electrochemically inert, its surface is not significantly affected by such stripping operation. In addition, a further advantage is obtained by the use of this anodic cleaning procedure since water is electrolyzed at sufficiently positive potentials to produce acid. This excess acid is created in the immediate vicinity of the electrode and is beneficial in solubilizing both electrochemically and non-electrochemically active deposits which are, in turn, dispersed away from an electrode surface through the ultrasonically produced cavitation to eliminate any effect on the amperometric measurement.

Referring to FIG. 2, there is seen a means by which electrochemical anodic cleaning may be achieved. A potential reversing timer 67 continuously switches the potential of the test electrode 20 between preestablished positive and negative values. For example, an advantageous time scale may utilize a one minute cycle with the anodic pulse continuously variable from 0 to about 30 seconds. During the interval that the anodic pulse is applied, the analog signal 61 from the demodulator is not usable, hence the normal signal must be stored in a holding circuit 63 during this interval. Simultaneous with the potential reversal, one may enable the ultrasonic cleaning oscillator 36. Thus, the timing device of the potential reversing timer 67 provides control signals for the potential reversing circuit therein, the holding circuit 63 and the ultrasonic oscillator 36. It will be understood that the frequency of potential reversal, the duration of the reversal and the level of the reverse potential may be adjusted for optimum electrode cleaning consistent with normal operation of the analyzer.

The ultrasonic cleaned flow temperature compensated amperometric analysis system and method of this invention finds application where amperometric analyzers are presently used but with considerable improvement in reliability of analysis. A particularly useful application is in bleach monitoring in the pulp and paper industry where satisfactory analysis of this type is currently not available.

I claim:

1. A system for flow compensated amperometric analysis of a flowing stream comprising:
   conduit means for enabling flow of the stream therethrough;
   electrode means to contact the stream flowing through said conduit means; said electrode means comprising means capable of serving as magnetic flow meter electrodes and as test and counter electrodes of an amperometric analysis system;
   a reference electrode positioned to contact the stream for printing a potentiostat with said electrode means serving as counter and test electrodes for amperometric measurement of the stream;
   means coupled to said electrodes to produce an amperometric measurement signal representing the current flow through said test electrode required to produce a predetermined potential difference between said reference and test electrodes;
   means coupled to said electrode means to develop magnetic flow metering signal representing the flow rate of said stream; and
   means for combining said magnetic flow metering signal with said amperometric measurement signal to obtain an amperometric analysis of the stream that is flow compensated.

2. A system for flow compensated amperometric analysis of a flowing stream as claimed in claim 1 wherein the potentiostat utilizes an isolated current source enabling the magnetic flow metering electrodes to serve simultaneously as the electrodes of the amperometric measurement circuit.

3. A system for flow compensated amperometric analysis of a flowing stream as claimed in claim 1 further including ultrasonic drivers mounted on the test and counter electrodes capable of activating the electrodes with sufficient amplitude to maintain them free of accumulating deposits which would affect the amperometric measurement.

4. A system for flow compensated amperometric analysis of a flowing stream as claimed in claim 3 further including means for applying an electrochemical anodic pulse to strip off accumulated electrode deposits electrochemically.

5. A system for flow compensated amperometric analysis of a flowing stream as claimed in claim 1 further including a thermistor means positioned in the system to contact the flowing stream for developing an output signal related to the temperature of the stream flowing through the cell and means for combining the output signal related to the stream temperature with the amperometric measurement to obtain an amperometric analysis of the stream that is temperature compensated.

6. A method for directly analyzing the concentration of unknown chemical species of a flowing stream by amperometric measurement comprising the steps of:
   flowing the stream through an amperometric cell containing electrode means comprising a test and a counter electrode and a reference electrode, said reference electrode having a potential relative to the test electrode;
   causing a current to flow between the test electrode and the counter electrode;
   developing an output signal related to said current to provide an amperometric measurement of the stream;
   applying a magnetic field to the flowing stream to develop from said electrode means a potential output signal related to stream flow rate through the cell; and
   combining the flow rate output signal and the amperometric output signal to obtain a final amperometric output signal relating to concentration of unknown chemical species in the stream that is flow compensated.

7. A method for directly analyzing the concentration of unknown chemical species of a flowing stream by amperometric measurement as claimed in claim 6 further including the steps of placing a resistance bulb sensor in the stream and obtaining therefrom an output signal relating to stream temperature; and
   combining the stream temperature output signal with the other output signals to obtain a final output signal which is also temperature compensated.

8. A method for directly analyzing the concentration of unknown chemical species of a flowing stream by amperometric measurement as claimed in claim 6, wherein the electrodes used for developing said flow rate output signal are also used as said test and counter electrodes.

9. A method for directly analyzing the concentration of unknown chemical species of a flowing stream by amperometric measurement as claimed in claim 6 further including the step of ultrasonically activating the test and counter electrodes to maintain them free from accumulating deposits which would affect the amperometric measurement.

10. A method for directly analyzing the concentration of unknown chemical species of a flowing stream by amperometric measurement as claimed in claim 9 further including the step of applying an electrochemical anodic pulse to strip off accumulated electrical deposits electrochemically.

* * * * *